United States Patent
Sun et al.

(10) Patent No.: US 12,133,874 B2
(45) Date of Patent: Nov. 5, 2024

(54) **APPLICATION OF BREAST MILK-DERIVED *LACTOBACILLUS REUTERI* IN REGULATING MATERNAL AND INFANT IMMUNE FUNCTION**

(71) Applicants: Fine (Hunan) Biotechnology Co., Ltd., Changsha (CN); Jin Sun, Wuxi (CN); Fine (Guangzhou) Biotechnology Co., Ltd., Guangzhou (CN)

(72) Inventors: Jin Sun, Wuxi (CN); Shuangqi Li, Changsha (CN); Ce Qi, Wuxi (CN); Mengfan Ding, Wuxi (CN)

(73) Assignees: Fine (Hunan) Biotechnology Co., Ltd., Changsha (CN); Jin Sun, Wuxi (CN); Fine (Guangzhou) Biotechnology Co., Ltd., Guangzhou (CN)

( * ) Notice: Subject to any disclaimer, the term of this patent is extended or adjusted under 35 U.S.C. 154(b) by 443 days.

(21) Appl. No.: 17/578,537

(22) Filed: Jan. 19, 2022

(65) Prior Publication Data
US 2022/0133820 A1 May 5, 2022

Related U.S. Application Data

(63) Continuation of application No. PCT/CN2020/080353, filed on Mar. 20, 2020.

(30) Foreign Application Priority Data

Jan. 23, 2020 (CN) .......................... 202010076261.7

(51) Int. Cl.
| | | |
|---|---|---|
| *A61K 39/02* | (2006.01) | |
| *A01N 63/00* | (2020.01) | |
| *A23L 33/135* | (2016.01) | |
| *A61K 35/747* | (2015.01) | |
| *A61P 37/04* | (2006.01) | |

(52) U.S. Cl.
CPC .......... *A61K 35/747* (2013.01); *A23L 33/135* (2016.08); *A61P 37/04* (2018.01)

(58) Field of Classification Search
None
See application file for complete search history.

(56) References Cited

FOREIGN PATENT DOCUMENTS

CN 110205261 A 9/2019

OTHER PUBLICATIONS

Li et al (Food & Function (Aug. 1, 2019 and online published Jun. 28, 2019), 10(8), 4705-4715).*
Lara-Villoslada et al (British Journal of Nutrition (2007), 98, Suppl. 1, S96-S100).*
Weizman et al (Pediatrics. 2005. Jan. 115(1): 5-9).*
Ding, Mengfan et al. "A study on human milk microbiota and their dominant lactic acid bacteria influening gut mucosal immune development in neonatal mice", Thesis, China Academic Journal electric publishing house, Dec. 31, 2019, english translation for abstract only. only abstract considered.

* cited by examiner

*Primary Examiner* — Jennifer E Graser
(74) *Attorney, Agent, or Firm* — IPRO, PLLC

(57) ABSTRACT

The disclosure discloses application of breast milk-derived *Lactobacillus reuteri* in regulating the maternal and infant immune function, belonging to the fields of microbiological technology and food science. The disclosure provides the effects of *Lactobacillus reuteri* Fn041 in enhancing the immunity of pregnant or lactating women and infants, i.e., enhancing the mucosal barrier, promoting the production of intestinal antibacterial peptides and IgA, promoting the development of the immune system of infants, preventing pathogen infection and reducing the incidence of allergic diseases.

16 Claims, 9 Drawing Sheets
Specification includes a Sequence Listing.

APPLICATION OF BREAST MILK-DERIVED *LACTOBACILLUS REUTERI* IN REGULATING MATERNAL AND INFANT IMMUNE FUNCTION

Technical Field

The disclosure relates to application of breast milk-derived *Lactobacillus reuteri* in regulating the maternal and infant immune function, belonging to the fields of microbiological technology and food science, and particularly relates to application of secretory immunoglobulin A coated *Lactobacillus reuteri* Fn041 from breast milk in promoting the gastrointestinal immune development of infants and enhancing the immunity of adults.

BACKGROUND

The initiation and maturation of the human immune system are closely related to intestinal microbes, and bacteria colonized in the intestinal tract in early infancy play an important role in this process. Breast milk is the main source of intestinal microbiota of healthy full-term infants. *Bifidobacterium* and *Lactobacillus* in breast milk can be continuously inoculated into intestinal tract of infants by breast-feeding to promote the development of normal intestinal microbiota. The normal intestinal microbiota of infants affects the intestinal immunity and protection of infants through various mechanisms. Firstly, the intestinal microbiota constitutes the first line of defense against pathogenic microorganisms, and can produce broad-spectrum antibacterial substances, and fermentation substrates competing with pathogenic bacteria, or competing for adhesion to intestinal mucin and other binding sites, thus inhibiting the colonization and growth of pathogenic microorganisms in infants' intestines, protecting infants against infection and promoting the maturation of immune system functions. Secondly, the intestinal microbiota of infants stimulates the gastrointestinal tract of newborns to initiate an immune response, promote the development of the immune system and reduce an inflammatory response. Due to the action of microorganisms from breast milk, the incidence of infectious diseases of infants fed breast milk is significantly lower than that of infants fed formula milk powder.

Some active bacteria in breast milk refer to that specific bacterium in mothers' intestinal tract migrate to the mammary gland through physiological ectopia. Mothers' intestine is rich in secretory immunoglobulin A (sIgA), which can selectively bind to specific bacteria. The sIgA coated bacteria can be recognized and ingested by M cells on the surfaces of intestinal Peyer's patches (PP), and transferred to dendritic cells (DC) in the PP to be carried into the mammary gland. After being ingested by infants, these bacteria can be combined with sIgA in the intestinal tract and be mediated into the intestinal PP to promote the development of immune cells in the PP, especially the maturation of IgA-producing plasma cells. The coating of bacteria with sIgA can promote the colonization of these bacteria in the mucosa, so that the bacteria can act on epithelial cells at a closer distance, and regulate the expression of tight junction proteins and antibacterial peptides in intestinal epithelial cells. *Lactobacillus* or *Bifidobacterium* coated with sIgA can be isolated from breast milk, which can induce the development of the immune system of infants after being ingested by lactating mothers or infants. Some studies have proved that sIgA derived from mothers' milk affects the composition and maturity of the intestinal microbiota of breast-fed infants, while infants mainly fed with formula milk lack sIgA, leading to excessively fast development of the intestinal microbiota. SlgA in breast milk mainly coates specific breast milk bacteria, affecting the development of intestinal bacteria in breast-fed infants. sIgA-coated lactic acid bacteria in breast milk are typical beneficial bacteria of healthy full-term infants, and are probiotic candidate strains suitable for infants, which can be used to promote the intestinal immune development of infants.

The World Health Organization, American Academy of Pediatrics, Chinese Nutrition Society, etc. all encourage mothers to extend breastfeeding time to at least one year or longer, and exclusive breastfeeding is strongly recommended for the first 6 months after birth. Some mothers have insufficient breast milk or are unsuitable for breastfeeding due to some reasons, so they have to choose formula milk powder as a supplement to breast milk, which hinders infants from getting bacteria from breast milk. There are significant regional differences in the bacterial composition of breast milk in China, and the content of beneficial bacteria in breast milk in some regions is obviously lower than that in other regions. Meanwhile, diseases during pregnancy such as eclampsia and gestational diabetes also cause breast milk microbiota to be different from healthy mothers, the transmission of which to infants may affect their health. In these cases, it is necessary to give probiotics supplements to infants to promote the healthy development of intestinal microbiota. Mothers ingesting sIgA-coacted beneficial bacteria isolated from breast milk can also enhance immunity, and these bacteria can transfer to breast milk and be ingested by infants through breastfeeding.

SUMMARY

The technical problem to be solved by the disclosure is to promote the development of intestinal immunity and ensure the intestinal barrier and protection function by means of probiotic supplements for infants who cannot be breastfed or infants who consume breast milk with disturbed microbiota and lactating women who need to enhance immunity.

To solve the above problem, the disclosure provides application of *Lactobacillus reuteri* Fn041 in preparing products for enhancing the immunity of a target population, increasing the expression and secretion of an intestinal antibacterial peptide, promoting the increase of numbers of immunoglobulin A (IgA) and intestinal IgA plasma cells, establishing or strengthening an intestinal barrier, and ability to killing pathogens such as *Salmonella*. The target population is pregnant women, lactating women and infants. The *Lactobacillus reuteri* Fn041 is *Lactobacillus reuteri* with the preservation number GDMCC No. 60546, which has been disclosed in the patent application document with the publication number CN110205261A.

In one embodiment, the products include, but are not limited to, food, medicine or health care products.

In one embodiment, the application is to prepare products with any one of the functions shown in (1) to (5):

(1) increasing the expression and secretion of the intestinal antibacterial peptide for pregnant or lactating women and infants;

(2) promoting the increase of numbers of intestinal IgA and intestinal IgA plasma cells for pregnant or lactating women and infants;

(3) enhancing the barrier function of intestinal mucosae of pregnant or lactating women and infants;

(4) promoting the development of the immune system of infants;

(5) enhancing the immunity of pregnant or lactating women; and (6) increasing the abundance of *Lactobacillus reuteri* in breast milk of lactating women.

In one embodiment, establishing or strengthening the intestinal barrier includes, but is not limited to: resisting the invasion of pathogenic bacteria, the pathogenic bacteria including *Salmonella*.

In one embodiment, the age of the infants is 0-36 months.

In one embodiment, food or medicine is provided to pregnant or lactating women or infants at a daily dose of $1\times10^4$ to $1\times10^{11}$, preferably $1\times10^7$ to $1\times10^{11}$ cfu of *Lactobacillus reuteri* Fn041.

In one embodiment, the *Lactobacillus reuteri* is added to a composition at a dose of $1\times10^4$ to $1\times10^{12}$ cfu/g dry matter to be provided to pregnant or lactating women or infants.

In one embodiment, *Lactobacillus reuteri* in the products is a living cell, an inactivated cell, a form of fermentation products or metabolites, or a mixture of any of the above forms.

In one embodiment, the product is food or medicine, whose dosage forms include, but are not limited to, tablets, capsules, solid powder or oral liquid.

In one embodiment, the product also contains prebiotics, and the prebiotics include, but are not limited to, one or more of inulin, fructooligosaccharides, short-chain fructooligosaccharides, galactooligosaccharides, human milk oligosaccharides or cow milk oligosaccharides.

In one embodiment, the food or medicine to which *Lactobacillus reuteri* Fn041 is added also contains, but is not limited to, one or more of the following components: prebiotics, *Euglena* powder or *Euglena* extract, *pericarpium citri reticulatae* powder or *pericarpium citri reticulatae* extract, huckleberry fruit powder or huckleberry fruit extract, wolfberry fruit powder or wolfberry fruit extract, fructus cannabis powder, fructus cannabis protein, milk protein, and animal and plant hydrolyzed protein or peptide. The prebiotics include, but are not limited to, inulin, fructooligosaccharides, short-chain fructooligosaccharides, galactooligosaccharides, human milk oligosaccharides or cow milk oligosaccharides or a combination of the above prebiotics.

Beneficial effects: The disclosure provides new application of *Lactobacillus reuteri* Fn041 in enhancing the immunity of infants and mothers, namely enhancing the mucosal barrier, promoting the production of the intestinal antibacterial peptide and IgA, and promoting the development of the immune system of infants.

For the young, animal experiments show that *Lactobacillus reuteri* Fn041 can promote the intestinal immune development of newborn mice and achieve the following effects:

(1) promoting the expression of genes of the antimicrobial peptide pathway in intestinal epithelial cells. The expression of the TLR4 gene is inhibited by about 0.5 times, and the expression of the TLR-9 gene is activated by 0.5-1 time;

(2) promoting the gene expression of the intestinal immunoglobulin A (IgA) pathway and the formation of IgA plasma cells, wherein the expression of CXCR5, CXCL13, APPIL, TGF-β and Foxp3 is increased by about one time;

(3) enhancing the expression of genes related to the intestinal mucosal barrier function, wherein the expression of ZO-2 and ZO-1 mRNA and mucin-2 can be increased by 0.5-3 times; and (4) increasing the intestinal villi to crypt depth ratio and enhancing the antimicrobial activity of crypt secretions, wherein a *Salmonella* inhibition rate of 50% can be achieved within 5 min.

For the mother, animal experiments show that *Lactobacillus reuteri* Fn041 can enhance the immunity of pregnant or dams, which is embodied as follows:

(1) increasing serum and intestinal antibody concentration, wherein serum IgA is increased from 11.97 ng/mL to 12.10 ng/mL, and IgE from 11.55 ng/mL to 11.73 ng/mL;

(2) promoting the number of cells producing mucosal antibodies, wherein the number of IgA plasma cells is increased by about one time;

(3) promoting the intestinal mucosal barrier and the expression of antimicrobial peptide related genes, wherein the expression intensity of PIgR, mucin-2 and occludin genes is increased by 0.5 times, 4 times and 1.4 times respectively; and (4) improving the morphology of intestinal villi and enhancing the resistance to pathogenic bacteria, wherein a *Salmonella* inhibition rate of 50% can be achieved within 10 min.

DETAILED DESCRIPTION

Figure 1A:
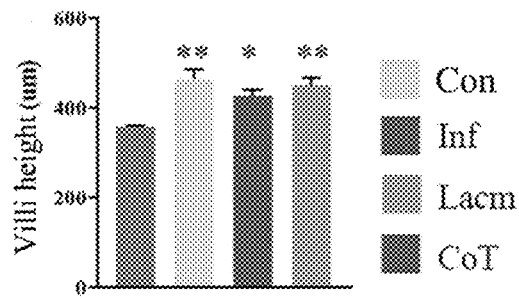
FIG. 1A shows the effect of *Lactobacillus reuteri* Fn041 treatment on the intestinal villi height.
Figure 1B:
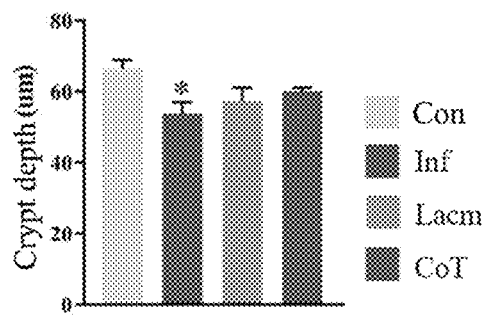
FIG. 1B shows the effect of *Lactobacillus reuteri* Fn041 treatment on the intestinal crypt depth.
Figure 1C:
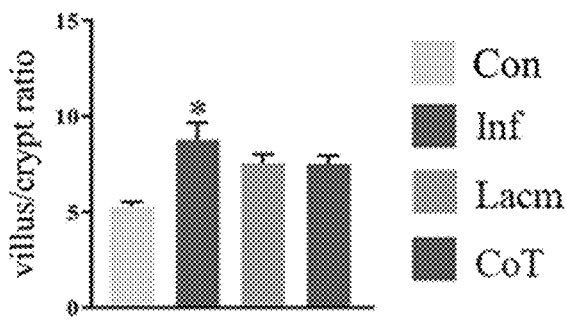
FIG. 1C shows the effect of *Lactobacillus reuteri* Fn041 treatment on the intestinal villi to crypt depth ratio.
Figure 1D:
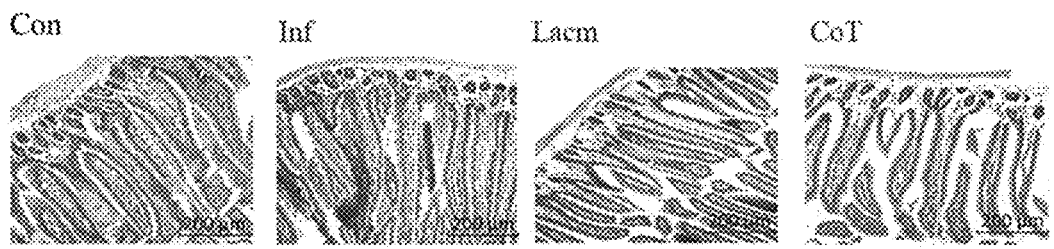
FIG. 1D shows the effect of *Lactobacillus reuteri* Fn041 treatment on the mucosal morphology of pups; From left to right are control, Inf, Lacm and CoT, wherein Inf indicates intragastric administration of *Lactobacillus* to pups, Lacm indicates intragastric administration of *Lactobacillus* to lactating dams, CoT indicates intragastric administration of *Lactobacillus* to both dams and pups, ** indicates a significant difference from the control group (p<0.01), and * indicates a significant difference from the control (P<0.05).

The disclosure will be further explained with specific examples below.

In the data analysis methods adopted in the following examples, experimental results are all expressed in (mean±standard deviation). SPSS 25.0 was used for statistical analysis of data, and one-way analysis of variance (ANOVA) and a Tukey test were used for comparison between groups. When the homogeneity of variance was less than 0.05, a nonparametric independent two-sample T test was conducted, and a Kruskal-Wallis test was used to analyze the data. Significant level: P<0.05, very significant level: P<0.01, and extremely significant level: P<0.001.

Example 1: Animal Experiment (1) Experimental Method

Animal grouping: 40 BALB/C female mice and 14 BALB/C male mice were fed with common feed at room temperature 22-24° C. and humidity 40-70% with the day and night cycle maintained at 8:00-20:00. The male mice and the female mice were separated for one week, and then put together according to a female to male ratio of 3:1 after one week. After the female mice were pregnant, the male mice were taken out. After the female mice gave birth, the dams were divided into two groups, one group was given normal saline (CON) through intragastric administration, the other group was given *Lactobacillus reuteri* Fn041 (1×10$^{10}$ CFU per mouse per day) through intragastric administration, and when pups reached 3 weeks old, they were weaned naturally. Each group of breast-fed male pups were divided into two groups, which were given normal saline or *Lactobacillus reuteri* respectively through intragastric administration. After 14 days, the treated pups were killed. The above pups were divided into: (1) Con group, in which both damsdams and pups were given normal saline through intragastric administration; (2) Inf group, in which the damsdams were given normal saline through intragastric administration, and the pups were given *Lactobacillus reuteri* Fn041 (1×10$^9$ CFU per mouse per day); (3) Lacm group, in which the damsdams were given *Lactobacillus reuteri* Fn041 (1×10$^{10}$ CFU per mouse per day) through intragastric administration, and the pups were given normal saline through intragastric administration; and (4) CO-T group, in which both damsdams and pups were given *Lactobacillus reuteri* Fn041 through intragastric administration, and the dose for the damsdams was 10$^{10}$ CFU per mouse per day and 10$^9$ CFU per mouse per day for pups.

Example 2 Immunohistochemical Analysis of Intestinal IgA$^+$ Plasma Cells (1) Dehydration: Intestine tissue was put into 50% ethanol, 75% ethanol, 85% ethanol and 90% ethanol respectively for shaking dehydration for 15 min, and then was put in 100% ethanol for treatment for 30 min, wherein the ethanol was replaced every 15 min.

(2) Transparentizing: Ethanol and n-butanol was mixed according to the ratio of 1:1 to obtain a mixed solution, the intestine tissue was put into the mixed solution, shaking was performed for 20 min, the liquid was poured out, and the intestine tissue was transferred to an n-butanol solution for treatment for 40 min, wherein n-butanol was replaced every 20 min.

(3) Wax immersion: Immersing was performed in 70° C. paraffin I for 3 h, and then transferring to 70° C. paraffin II was performed for immersion for 3 h.

(4) Embedding: The intestine tissue treated in step (3) was embedded in paraffin.

(5) Slicing: Jejunum tissue was sliced into pieces with a thickness of 5 μm with a Leica microtome, the pieces were spread in a water bath at 42° C., and the pieces were baked at 70° C. for 30 min.

(6) Dewaxing and hydration: Soaking was performed in xylene three times, each time lasting 5 min; soaking was performed in 100% ethanol twice, each time lasting 5 min; soaking was performed in 95% ethanol, 85% ethanol and 75% ethanol sequentially for 3 min respectively; and then washing with deionized water was performed for 5 min.

(7) Antigen repair: 200 mL of EDTA buffer solution with pH 9.0 was added into a dyeing box, the tissue slices after dewaxing and hydration were placed on a plastic slice rack of the dyeing box, heating was performed in an autoclave till saturation, then continuing heating was performed for 5 min, a power supply was turned off, the dyeing box was taken out after 10 min, the dyeing box was cooled at room temperature for 30 min, and the dyeing box was soaked in a PBS buffer solution for 3 min×3 times.

(8) 100 μL of 3% $H_2O_2$ was added to each slice, incubating at room temperature was performed for 10 min, and soaking was performed in PBS for 3 min×3 times.

(9) The PBS buffer solution was removed, 100 μL of 2.5% goat serum was added, incubating at room temperature was performed for 30 min, and a blocking solution was removed.

(10) 100 μL of diluted rabbit anti-mouse IgA monoclonal antibody (primary antibody) was added to each slice, incubating was performed at 25° C. for 1 h, and soaking was performed in PBS for 3 min×3 times.

(11) PBS was removed, 100 μL of goat anti-rabbit IgG monoclonal antibody (secondary antibody) was added, incubating was performed at 25° C. for 30 min, and soaking was performed in PBS for 3 min×3 times.

(12) PBS was removed, 100 μL of DAB color developing solution prepared in real time was added, color development was performed under a microscope for 5 min, and the reaction was stopped with tap water.

(13) Redyeing was performed with hematoxylin for 12 sec and tap water was used for rinsing.

(14) Differentiating was performed with 1% hydrochloric acid alcohol for 1 sec, tap water was used for washing, and returning to blue with tap water was performed for 5 min.

(15) Dehydration and transparentizing: treating was performed with 75% ethanol, 85% ethanol and 95% ethanol respectively for 3 min, then treating was performed with 100% ethanol for 5 min, the operation was repeated three times, and then soaking was performed in xylene for 5 min and then 3 min.

(16) Sealing with neutral gum and baking in an oven at 60° C. for 20 min were performed.

An eyepiece of a microscope was inverted by 10 times and an objective lens 20 times, and after observation and photo shooting, and Image-Pro Plus software was used for imaging analysis. The mean optical density (density (mean)) was calculated, density (mean)=integrated optical density (IOD)/area. The mean number of plasma cells contained in each villus was counted with the microscope.

Figure 2A:
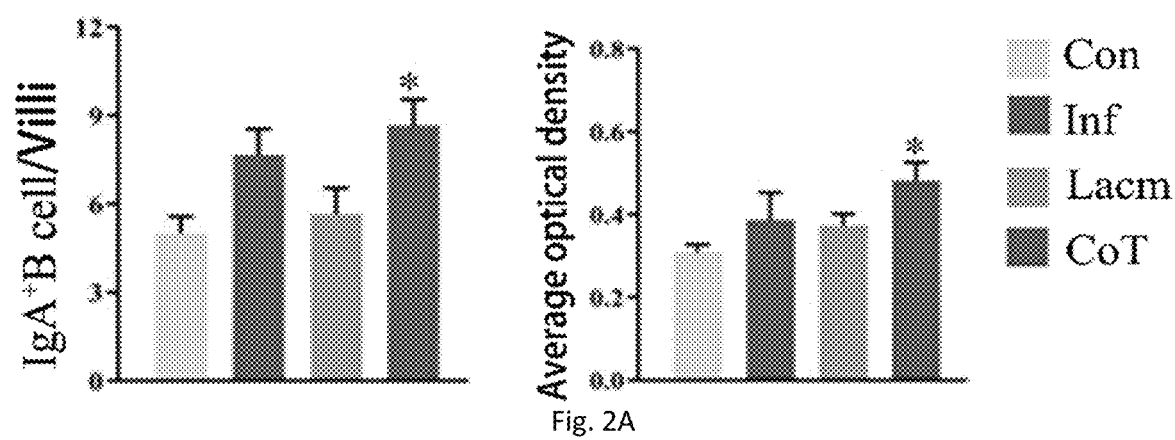
FIG. 2A shows the effect of *Lactobacillus reuteri* Fn041 treatment on the number of IgA plasma cells in the intestinal mucosa of pups, including the average number of IgA$^+$ cells per unit vill and an optical density per unit area
Figure 2B:
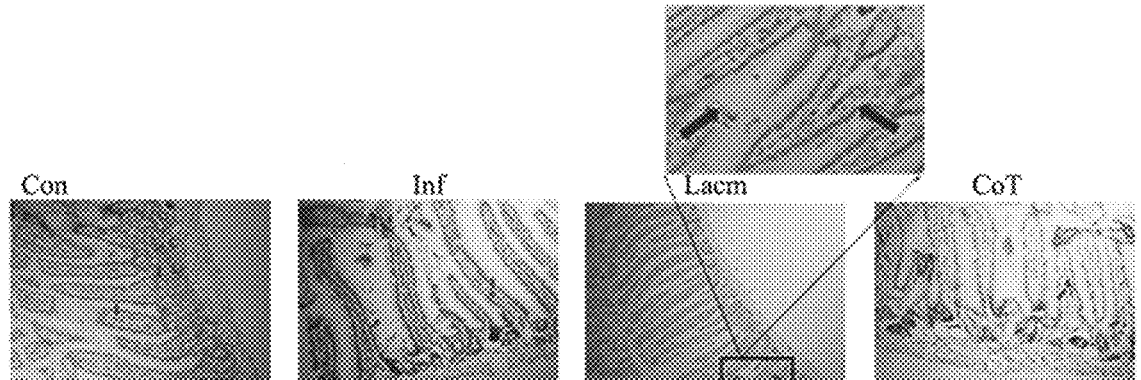
FIG. 2B shows a typical immunohistochemical staining pattern; from left to right are control, Inf, Lacm and CoT, wherein Inf indicates intragastric administration of *Lactobacillus* to pups, Lacm indicates intragastric administration of *Lactobacillus* to dams, CoT indicates intragastric administration of *Lactobacillus* to both dams and pups, and * indicates a significant difference from the control (P<0.05).

The villi height to crypt depth ratio can comprehensively reflect the digestion and absorption function of intestines. The higher the villi, the larger the intestinal surface area and the stronger the intestinal absorption function. The intestinal crypt depth represents the cell production rate. The shallower the crypt, the better the cell maturity and the more mature the secretion function. FIG. 1 shows that the villi height to crypt depth ratio is significantly increased after pups ingest *Lactobacillus reuteri* (p<0.01), and the villi height to crypt depth ratio can also be increased by giving *Lactobacillus reuteri* to dams (p<0.05), indicating that *Lactobacillus reuteri* promotes the intestinal absorption function and crypt cell maturation, and the content of IgA plasma cells in villi can be significantly increased by breast milk combined with intragastric administration to pups (FIG. 2) (p<0.05).

Example 3 Expression and Antibacterial Activity of Antimicrobial Peptide Genes in Intestinal Epithelial Cells of Pups RNA extraction and cDNA preparation of jejunum and intestine Peyer's patch, comprising the following steps: taking out the liver and spleen of mice in an ultra-clean table, cutting off 0.1 g of jejunum and putting it into Trizol quickly, extracting RNA from the jejunum and Peyer's patch by a Trizol method, determining $OD_{260/280}$ and concentration by NanoDrop, adjusting the RNA concentration to 1,000 ng/μL, making $OD_{260/280}$ within the range of 1.8-2.0, conducting reverse transcription of RNA according to reaction systems in Table 1, mixing with the reaction system in step 1 evenly and then bathing in ice at 70° C. for 5 min, then mixing with the second system evenly and bathing in water at 37° C. for 1 h and in ice at 95° C. for 3 min, and storing the cDNA after reverse transcription at −80° C.

Reverse transcription fluorescence quantitative PCR in jejunum (RT-PCR), comprising the following steps: conducting quantitative PCR analysis by using cDNA after reverse transcription in jejunum as an amplification template, wherein the reaction system: 2×SYBR Rreen Master Mix 5 μL, 0.4 μL for upstream primer and 0.4 μL for downstream primer (10 μM, see Table 2 for sequence), cDNA 0.3 μL, and DEPC water 3.7 μL; amplification conditions: 95° C., 5 min; 95° C., 20 sec; 60° C., 30 sec; 72° C., 1 min, 40 cycles, 72° C., 2 min; and using β-actin as internal reference, and analyzing the data by a 2-ΔΔCt method.

TABLE 1

Reverse transcription reaction system

| | Reagent | Volume (μL) | Concentration |
|---|---|---|---|
| Step 1 (10 μL system) | RNA | 2 | 1000 ng/μL |
| | dNTP | 2 | 10 mM |
| | Oligo (dT) | 1.5 | 10 mM |
| | DEPC water | 4.5 | |
| Step 2 (10 μL + 15 μL system) | 5× reverse transcription buffer | 5 | |
| | Rnaase inhibitor | 0.25 | 50 U/μL |
| | M-MLV reverse transcriptase | 0.5 | 200 U/μL |
| | DEPC water | 9.25 | |

TABLE 2

Real-time fluorescence quantitative RT-PCR primer

| Gene name | Sequence | Serial table number |
|---|---|---|
| Epithelial cell mucosal barrier related genes | | |
| β-actin | F: TGACGTTGACATCCGTAAAGACC; R: CTCAGGAGGAGCAATGATCTTGA | SEQ ID NO: 1/2 |
| ZO-1 | F: TACCTCTTGAGCCTTGAACTT; R: CGTGCTGATGTGCCATAATA | SEQ ID NO: 3/4 |
| ZO-2 | F: GCCAAAACCCAGAACAAAGA; R: ACTGCTCTCTCCCACCTCCT | SEQ ID NO: 5/6 |

TABLE 2-continued

Real-time fluorescence quantitative RT-PCR primer

| Gene name | Sequence | Serial table number |
|---|---|---|
| Occludin | F: GTGTGGTTGATCCCCAGGAG; <br> R: TCGCTTGCCATTCACTTTGC | SEQ ID NO: 7/8 |
| Claudin-2 | F: CCCAGGCCATGATGGTGA; <br> R: TCATGCCCACCACAGAGATAAT | SEQ ID NO: 9/10 |
| PlgR | F: AGTAACCGAGGCCTGTCCTT; <br> R: GTCACTCGGCAACTCAGGA | SEQ ID NO: 11/12 |
| MUC2 | F: CCCAGAAGGGACTGTGTATG; <br> R: TGCAGACACACTGCTCACA | SEQ ID NO: 13/14 |
| Peyer's patch IgA plasma cell induction pathway | | |
| CXCR5 | F: ATGAACTACCCACTAACCCTGG; <br> R: TGTAGGGGAATCTCCGTGCT | SEQ ID NO: 15/16 |
| CXCL13 | F: GGCCACGGTATTCTGGAAGC; <br> R: GGGCGTAACTTGAATCCGATCTA | SEQ ID NO: 17/18 |
| APRIL | F: CTTTCGGTTGCTCTTTGGTTG; <br> R: CGACAGCACAAGTCACAGC | SEQ ID NO: 19/20 |
| TGF-β | F: CTCCCGTGGCTTCTAGTGC; <br> R: GCCTTAGTTTGGACAGGATCTG | SEQ ID NO: 21/22 |
| Foxp3 | F: CCCATCCCCAGGAGTCTTG; <br> R: ACCATGACTAGGGGCACTGTA | SEQ ID NO: 23/24 |
| Intestinal antimicrobial peptide production pathway genes | | |
| TLR2 | F: AAAATGTCGTTCAAGGAG; <br> R: TTGCTGAAGAGGACTGTT | SEQ ID NO: 25/26 |
| TLR4 | F: GGAACAAACAGCCTGAGACAC; <br> R: CAAGGGATAAGAACGCTGAGAA | SEQ ID NO: 27/28 |
| TLR9 | F: GGTGTGGAACATCATTCT; <br> R: ATACGGTTGGAGATCAAG | SEQ ID NO: 29/30 |
| MyD88 | F: TGGCATGCCTCCATCATAGTTAACC; <br> R: GTCAGAAACAACCACCACCATGC | SEQ ID NO: 31/32 |
| NF-kB | F: AGGCTTCTGGGCCTTATGTG; <br> R: TGCTTCTCTCGCCAGGAATAC | SEQ ID NO: 33/34 |
| CRS1C | F: TGCTCTTCAAGATGTAGCCCAACG; <br> R: TGGAGCTTGGGTGGTGATTGCA | SEQ ID NO: 35/36 |
| CRS4C | F: GCATGGAATCTGGGTCAAGATAAC; <br> R: AGAAGGAAGAGCAATCAAGGCTAAG | SEQ ID NO: 37/38 |
| RegIII-γ | F: TTCCTGTCCTCCATGATCAAAA; <br> R: CATCCACCTCTGTTGGGTTCA | SEQ ID NO: 39/40 |
| a-defensin | F: ATCATCCAGGTGATTCCCAGCCAT; <br> R: TTCCGGGTCTCCAAAGGAAACAGA | SEQ ID NO: 41/42 |

Preparation of intestine crypt and evaluation of antibacterial activity of antibacterial peptide, comprising the following steps: washing a segment of intestine cavity of mice with precooled sterile water, everting the intestinal segment and shaking in a PBS buffer containing 30 mM EDTA without $Ca^{++}$ and $Mg^{++}$ to elute the crypts, eluting the villi and crypts several times at 5 min intervals, conducting centrifugation (700 g), resuspending in the PBS buffer, transferring a single crypt into a silicified microcentrifuge tube with a capillary pipette, estimating about 1000 crypts by a blood cell counting method, resuspending in 2 ml of iPIPES buffer (10 mM PIPES+137 mM NaCl, pH 7.4), adding Salmonella at 1000 CFU/crypt, incubating at 37° C. for 30 min, conducting centrifugation on the crypts, take 10 μl of supernatant, spreading it on a nutrient agar plate, determining the colony number after growing overnight, and measuring the germicidal rates for 1, 2.5, 5, 10, 15 and 30 min respectively.

Figure 3:
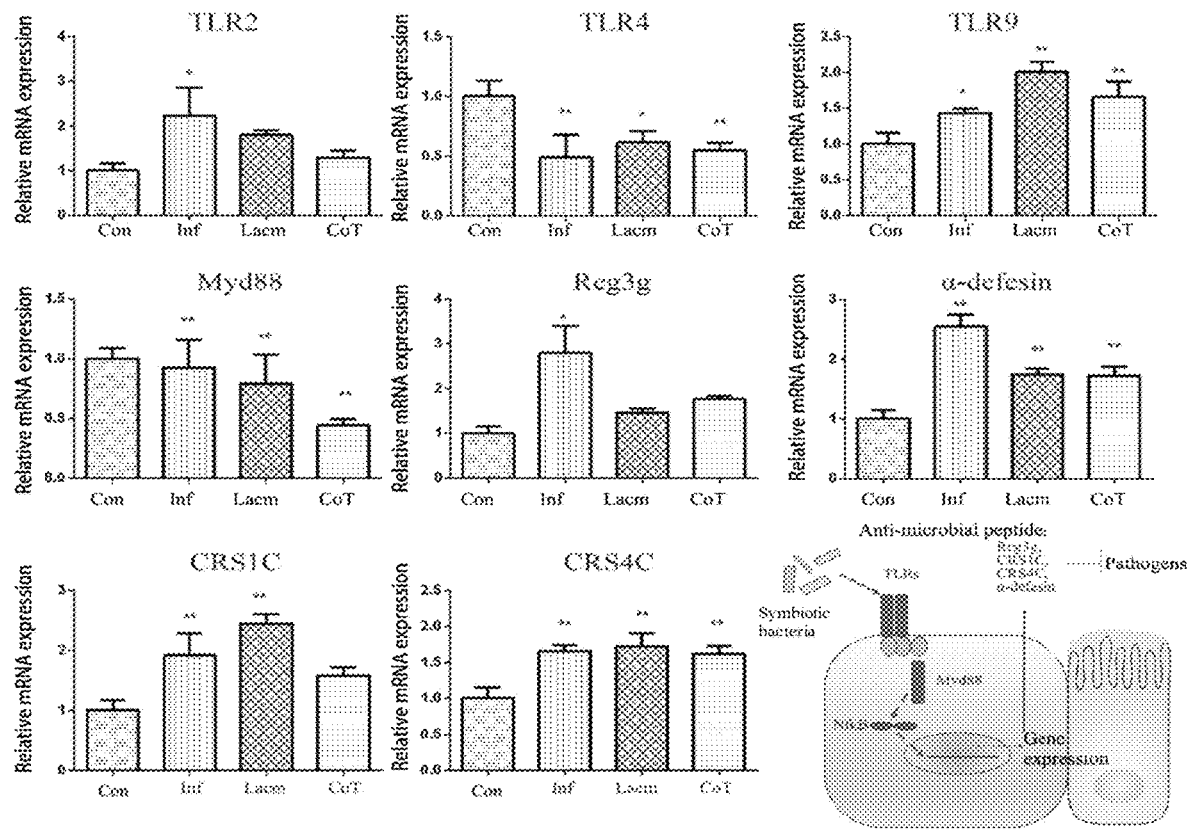
FIG. 3 shows the effect of *Lactobacillus reuteri* Fn041 treatment on the gene expression of the intestinal antimicrobial peptide pathway in pups. Inf indicates intragastric administration of *Lactobacillus* to pups, Lacm indicates intragastric administration of *Lactobacillus* to dams, CoT indicates intragastric administration of *Lactobacillus* to both dams and pups, ** indicates a significant difference from the control (p<0.01), and * indicates a significant difference from the control (P<0.05).

The antimicrobial peptide expressed by Paneth cells at the base of the intestinal crypt is an important defensive molecule in the intestinal tract, which is secreted into the intestinal mucus layer to resist the invasion of pathogenic bacteria and potentially pathogenic symbiotic bacteria. Peptidoglycan, endotoxin, bacterial DNA released by bacterial cells are combined with toll-like receptors (TLR2, TLR4, TLR9, etc.) of Paneth cells, and through signal transduction mediated by transducing protein MyD88, Nf-κB sub-protein in cytoplasm can be released, enter cells and induce a variety of antimicrobial expressions. FIG. 3 shows that the expression of the TLR4 gene in the intestine of the three groups of mice was significantly inhibited by about 0.5 times, and the expression of the TLR-9 gene was activated by 0.5-1 time respectively ($p<0.05$), and the expression of TLR2 was significantly increased by direct intragastric administration to pups, which was twice as high as that of the control ($p<0.05$). Besides, all the three treatments inhibited the expression of Myd88 ($p<0.05$), and significantly induced the expression of α-defense peptide, CRS1C and CRS4C. The expression of reg3g and CRS1C was also significantly induced by direct intragastric administration to pups, and the expression of Reg3g and a-defensin was even increased by 2 times and 1.5 times respectively ($p<0.05$).

Figure 4:
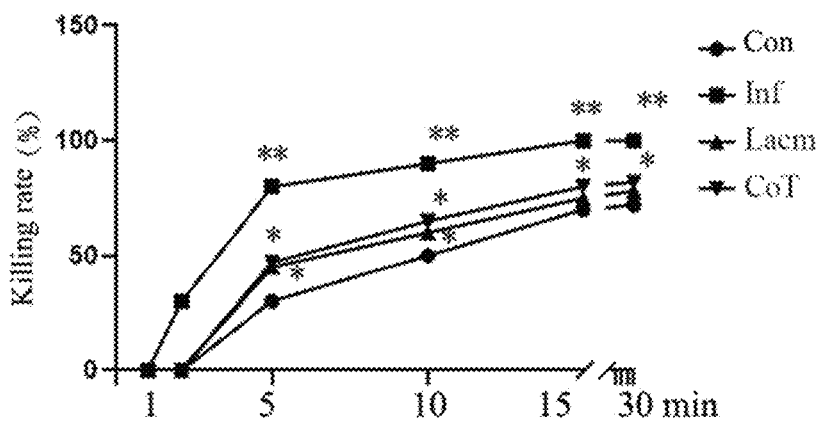
FIG. 4 shows the effect of *Lactobacillus reuteri* Fn041 treatment on the bactericidal activity of the intestinal crypt in pups. Inf indicates intragastric administration of *Lactobacillus* to pups, Lacm indicates intragastric administration of *Lactobacillus* to dams, CoT indicates intragastric administration of *Lactobacillus* to both dams and pups, ** indicates a significant difference from the control (p<0.01), and * indicates a significant difference from the control (P<0.05).

FIG. 4 shows that treating the intestinal crypt cells of mice in three ways also significantly inhibited Salmonella. A lethal rate of 50% can be achieved within 5 min simply by treating the secretions of 1000 crypts of pups, and a lethal rate of 50% for Salmonella can be achieved within 10 min by treating the damsdams or the damsdams and pups simultaneously. The bacteriostatic effect was significantly higher than that of the control.

Example 4 Intestinal Peyer's Patch IgA Gene Expression in Pups

IgA is the most important active molecule of the intestinal immune system, which is mainly released into the mucous layer in the form of secretory IgA (sIgA) to restrain the excessive proliferation and migration of pathogenic bacteria. Intestinal Peyer's patch is the initial induction site of IgA plasma cells. Bacteria are absorbed by M cells of the Peyer's patch and then transmitted to dendritic cells (DC), so as to activate DC, induce follicular dendritic cells (FDC) to produce TGFβ1 and CLCL13 through TLR and FDC, and promote Foxp3-T cells to transform into follicular helper T(Tfh) cells, which express CXCR5. Under the participation of TGFβ, the antibodies expressed by initial IgM$^+$ B cells undergo class conversion and are differentiated into IgA$^+$ B cells. After migrating to the lamina propria, these cells are transformed into IgA plasma cells, which can produce and secrete IgA. IgM$^+$ cells in the lamina propria can be transformed into IgA$^+$ cells under the action of APPIL on the premise that the intestinal immune function is mature.

Figure 5:
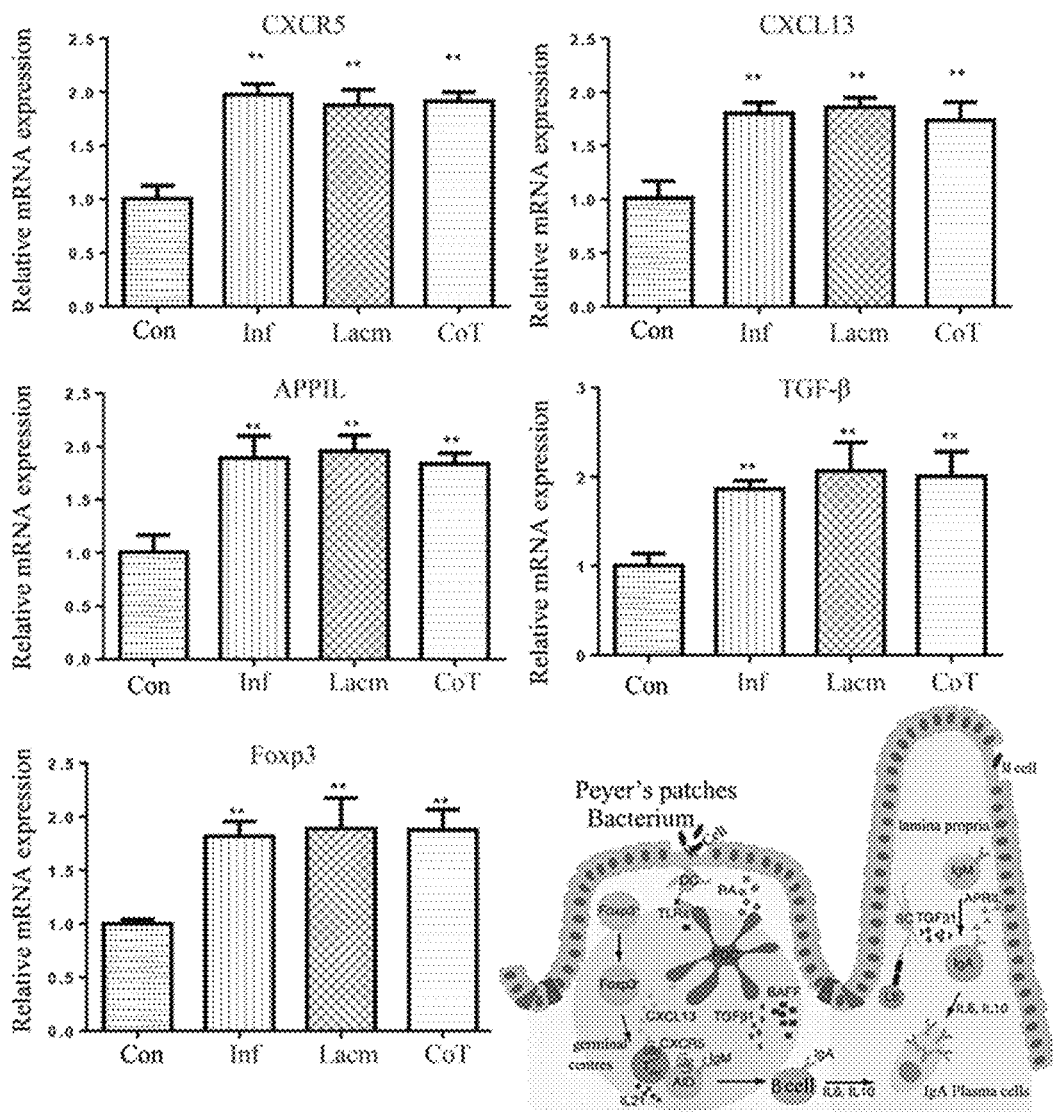
FIG. 5 shows the effect of *Lactobacillus reuteri* Fn041 treatment on intestinal Peyer's patch IgA$^+$ cell production pathway gene expression in pups. Inf indicates intragastric administration of *Lactobacillus* to pups, Lacm indicates intragastric administration of *Lactobacillus* to dams, CoT indicates intragastric administration of *Lactobacillus* to both dams and pups, ** indicates a significant difference from the control (p<0.01), and * indicates a significant difference from the control (P<0.05).

RNA extraction and fluorescent quantitative PCR (RT-PCR) were carried out according to the method of Example 3. Results are shown in FIG. 5. The expression of Peyer's patch CXCR5, CXCL13, APPIL, TGF-β and Foxp3 were significantly induced by treating pups or damsdams separately or simultaneously ($P<0.01$), and the expression was increased by about one time. The results indicate that

*Lactobacillus reuteri* treatment causes Foxp3⁺T to become intestinal chemotaxis and participate in the production of IgA⁺ plasma cells.

Example 5 Expression of Intestinal Mucosal Barrier Related Genes in Pups Corresponding to Different Treatments According to the grouping of Example 1, an animal experiment was carried out. The mice were given 4 kDa fluorescein isothiocyanate-dextran (FD4, 125 mg/mL) (600 mg/kg body weight) through intragastric administration. After 4 hours, the eyeballs were taken for blood collection, and all treatments after blood collection needed to be protected from light. Blood was incubated at room temperature (RT) for at least 1 h to coagulate blood, and high-speed centrifugation was conducted for 10 min to separate serum. Serum aliquot was diluted with PBS 1:1 in duplicate, and fluorescence readings at 488/530 nm were analyzed. The concentration of FD4 in serum samples was determined according to the FD4 standard curve value of PBS continuous dilution. The control mouse serum of FD4 in all the serum samples was standardized.

Figure 6:
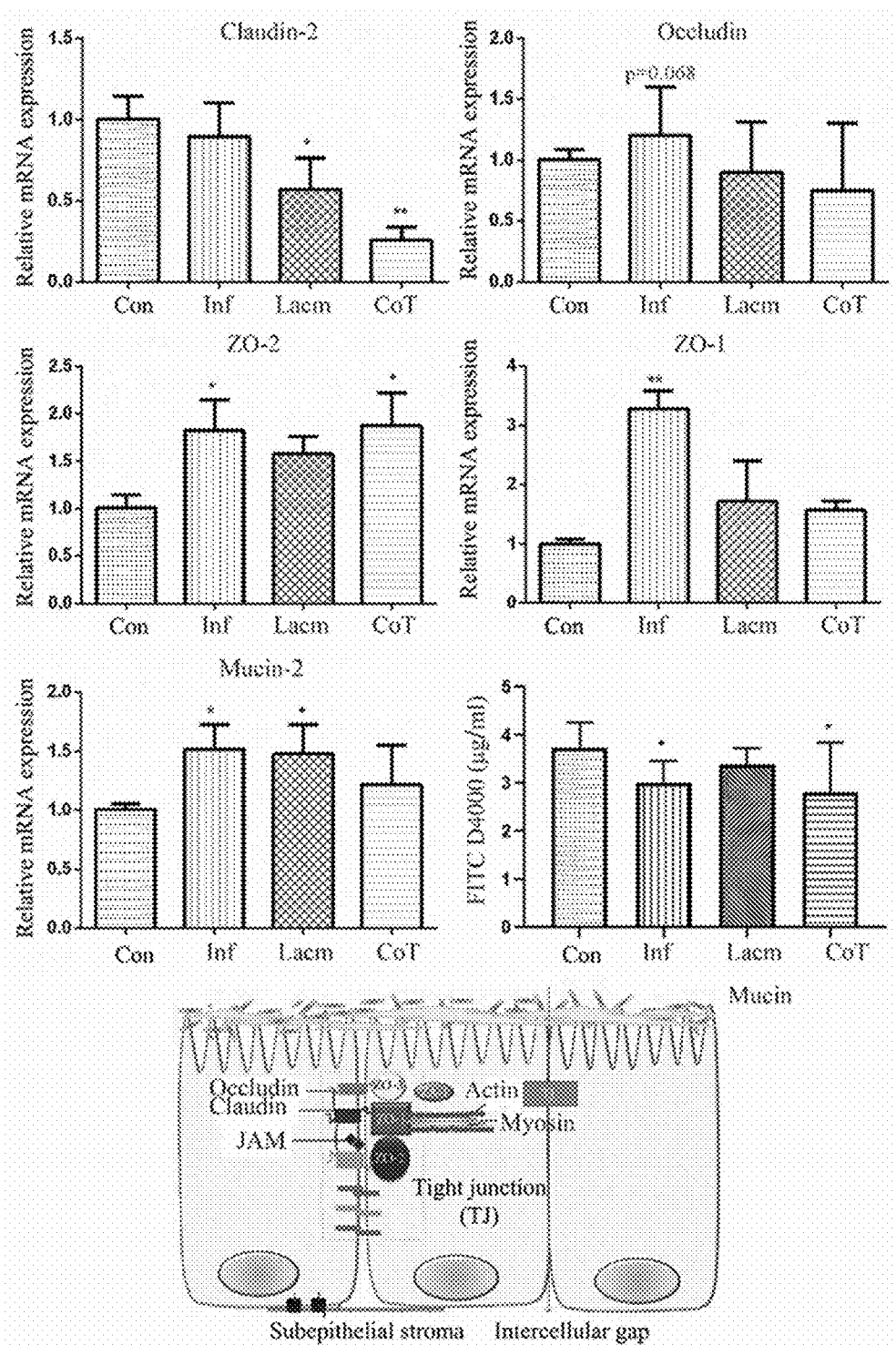
FIG. 6 shows the effect of *Lactobacillus reuteri* Fn041 treatment on the expression of intestinal mucosal barrier related genes in pups. Inf indicates intragastric administration of *Lactobacillus* to pups, Lacm indicates intragastric administration of *Lactobacillus* to dams, CoT indicates intragastric administration of *Lactobacillus* to both dams and pups, ** indicates a significant difference from the control (p<0.01), and * indicates a significant difference from the control (P<0.05).

As shown in FIG. 6, the concentration of FD4 in blood decreased by all three treatments, indicating that the permeability of the mucous membrane of pups was improved, and the concentration of FD4 could be reduced by at least 20% by treating only pups and treating pups and damsdams simultaneously.

The first line of defense against symbiotic bacteria and pathogenic bacteria in infants' intestines is the intestinal mucosal barrier, and this physical barrier includes biochemical and immune components. The physical barrier is mainly composed of intestinal epithelial cells through tight junctions, and the chemical barrier is mainly composed of mucus covering the intestinal surface. The tight junction is a complex composed of intracellular zona occludens (ZO1), Claudin, and intercellular Occludin. The expression of Claudin-2 was down-regulated and the expression of ZO1 and Occludin genes was up-regulated when the mucosal barrier weakened. Mucus is mainly composed of mucin 2 expressed by epithelial cells, and its enhanced expression is beneficial to the maintenance of the mucus barrier.

FIG. 6 shows that pups ingesting *Lactobacillus reuteri* Fn041 can significantly up-regulate the expression of ZO-2 and ZO-1 mRNA and mucin-2, and the increase amount can reach 0.5-3 times. Claudin-2 can be significantly inhibited and mucin-2 mRNA can be induced after damsdams ingest *Lactobacillus reuteri*, which indicates that ingestion of *Lactobacillus reuteri* Fn041 in different ways can improve the mucosal barrier.

Example 6 Effects of Different Treatments on Intestinal Immune Function, Intestinal Morphology and Mucosal Barrier of Damsdams Intestine tissue was treated according to the method of Example 1, and the content of sIgA in the intestine of the damsdams was determined strictly according to the instructions of sIgA ELISA kit.

Figure 7:
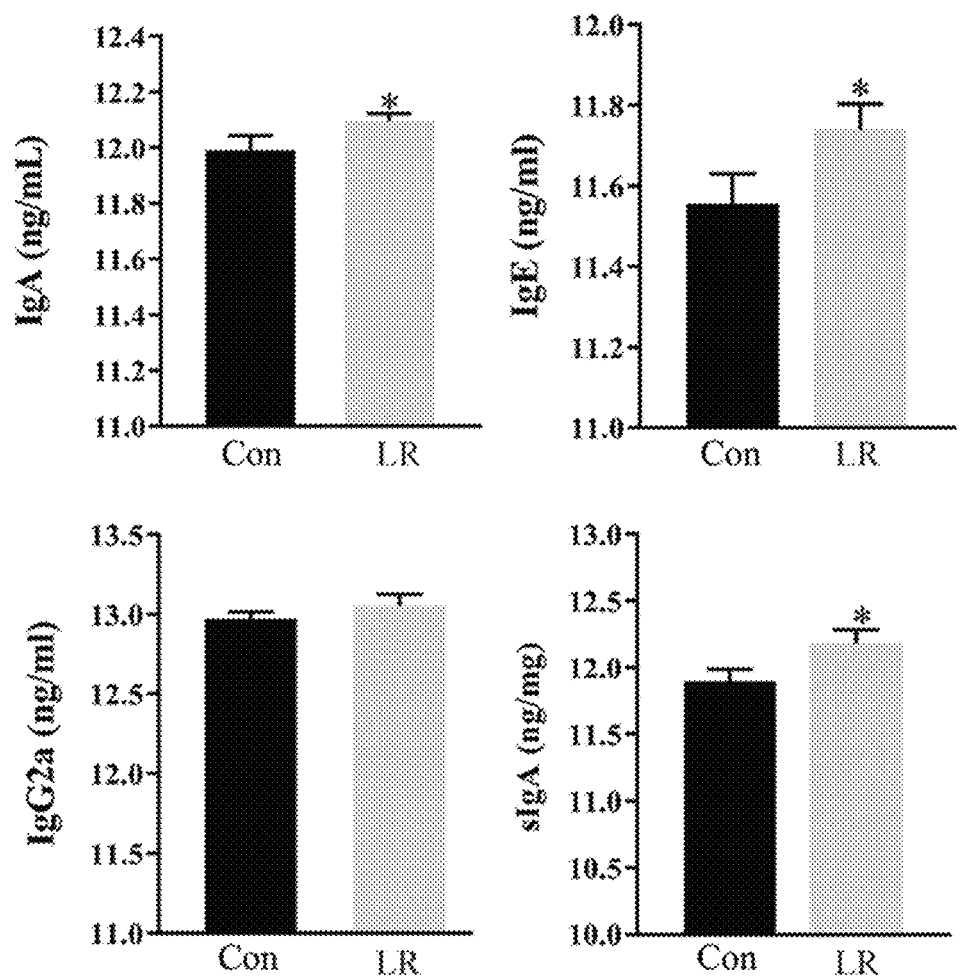
FIG. 7 shows the effect of *Lactobacillus reuteri* Fn041 treatment on serum IgA, IgE, IgG2a and intestinal sIgA antibody concentration in adult female mice. Control indicates a control group, LR indicates a *Lactobacillus reuteri* Fn041 treatment group, and * indicates a significant difference between the two groups after a T test (p<0.05).
Figure 8:
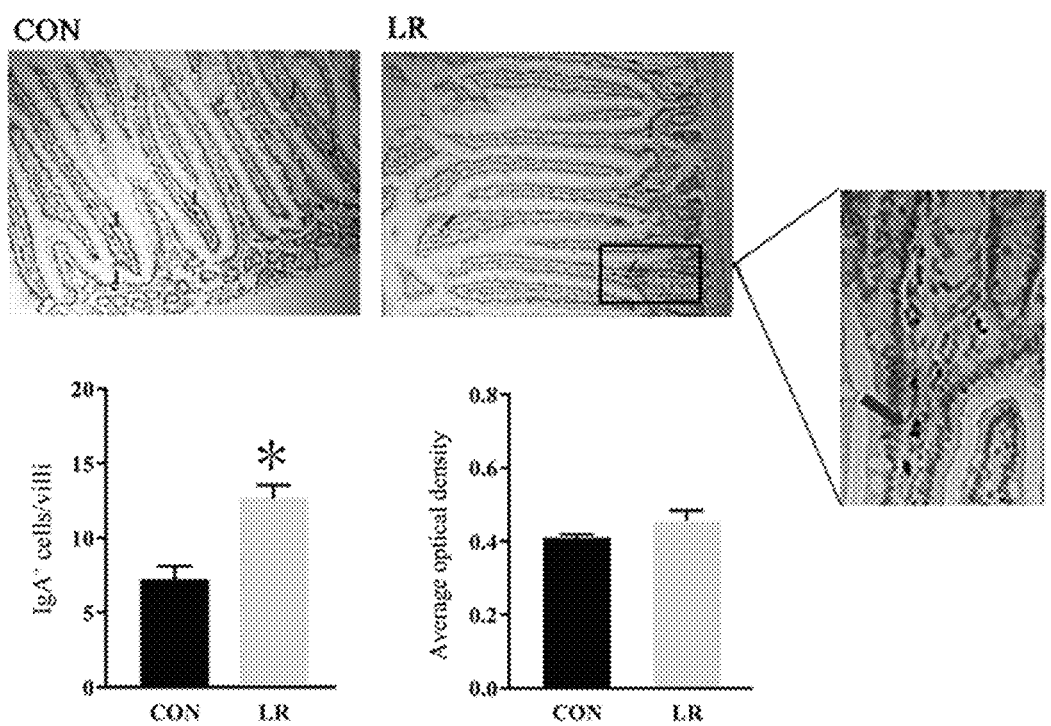
FIG. 8 shows the effect of *Lactobacillus reuteri* Fn041 treatment on IgA plasma cell content in the lamina propria of intestinal villi of adult female mice. CON indicates a control group, LR indicates a *Lactobacillus reuteri* Fn041 treatment group, and * indicates a significant difference between the two groups after a T test (p<0.05).
Figure 9:
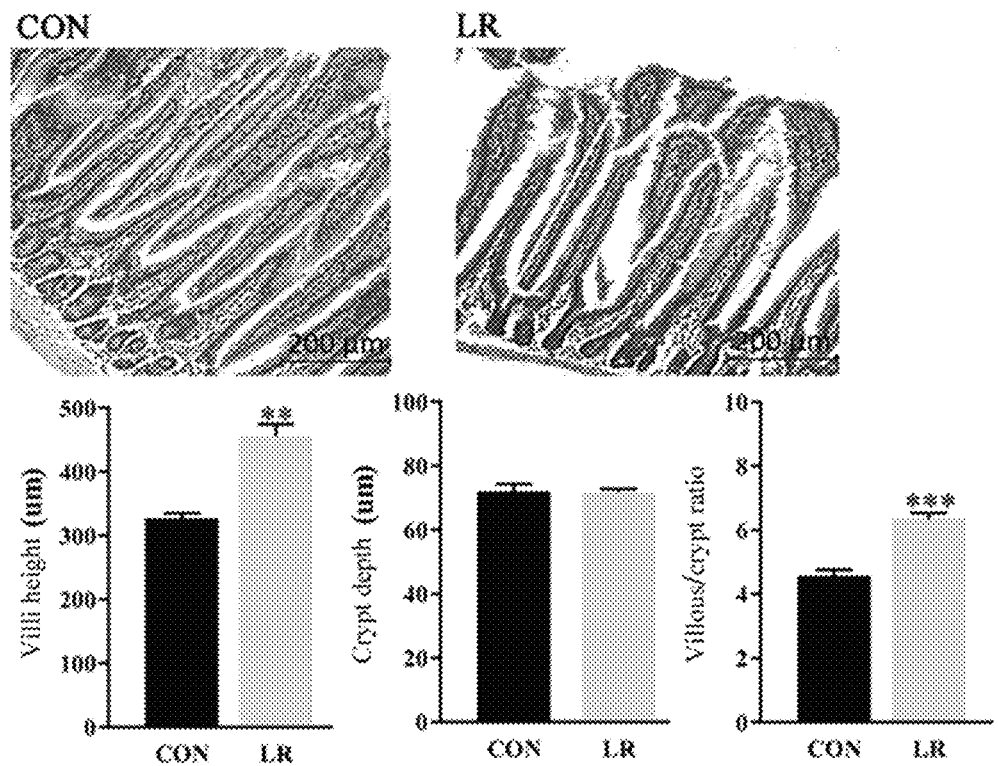
FIG. 9 shows the effect of *Lactobacillus reuteri* Fn041 treatment on the morphology of intestinal villi of adult female mice. CON indicates a control group, LR indicates a *Lactobacillus reuteri* Fn041 treatment group, a significant difference is shown between the two groups after a T test, p<0.01, and *p<0.001.
Figure 10:
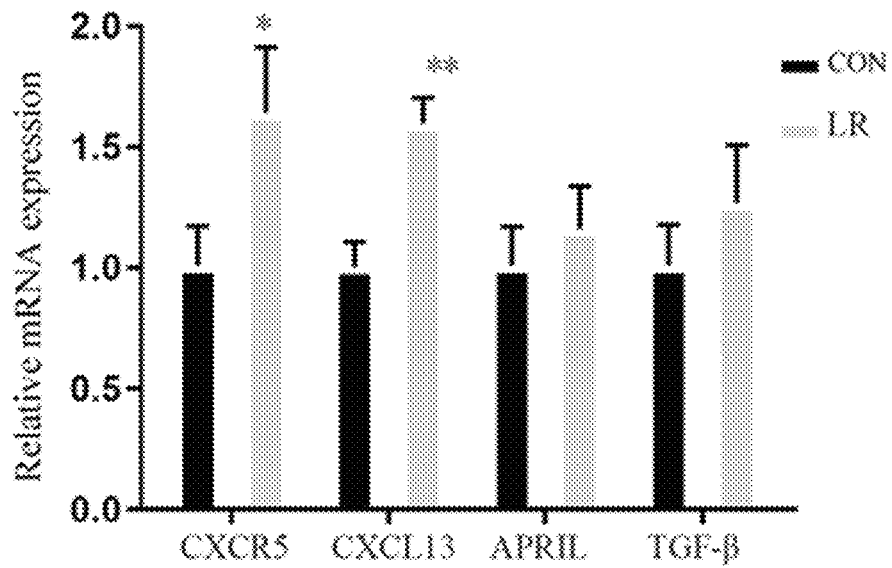
FIG. 10 shows the effect of *Lactobacillus reuteri* Fn041 treatment on intestinal Peyer's patch IgA$^+$ cell production pathway gene expression in adult female mice. Control indicates a control group, LR indicates a *Lactobacillus reuteri* Fn041 treatment group, a significant difference is shown between the two groups after a T test, *p<0.05, and ***p<0.01.
Figure 11:
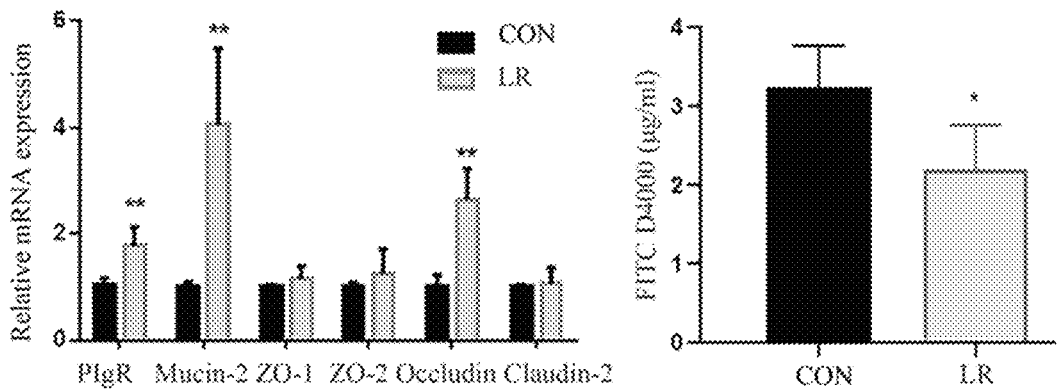
FIG. 11 shows the effect of *Lactobacillus reuteri* Fn041 treatment on the expression of intestinal mucosal barrier related genes in adult female mice. Control indicates a control group, LR indicates a *Lactobacillus reuteri* Fn041 treatment group, a significant difference is shown after a Ttest, and **p<0.01.
Figure 12:
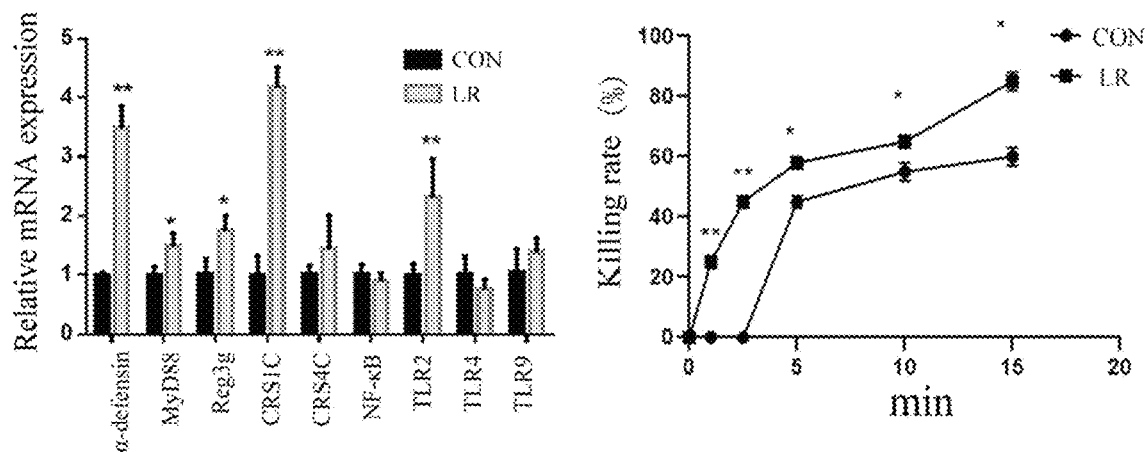
FIG. 12 shows the effect of *Lactobacillus reuteri* Fn041 treatment on gene expression of the intestinal antimicrobial peptide pathway in adult female mice. Control indicates a control group, LR indicates a *Lactobacillus reuteri* Fn041 treatment group, a significant difference in the antibacterial peptide is shown after a T test, *p<0.05, and ***p<0.01.

After treatment with *Lactobacillus reuteri*, serum IgA, IgE and intestinal sIgA of the damsdams increased significantly ($p<0.05$) (FIG. 7). Serum IgA increased from 11.97 ng/mL to 12.10 ng/mL, and IgE increased from 11.55 ng/mL to 11.73 ng/mL, indicating that mucosal immunity and systemic immunity were both enhanced. Besides, the number of IgA plasma cells in the lamina propria of the intestine of the damsdams increased by about one time ($p<0.05$, FIG. 8), and the expression of two genes CXCR5 ($p<0.05$) and CXCL13 ($p<0.01$) related to IgA plasma cell transformation in the Peyer's patch of the intestine increased significantly (FIG. 10), which further indicate that mucosal immunity was enhanced, so as to prevent bacterial infection and diarrhea and prevent allergic diseases such as eczema. FIG. 9 shows that after treating breast milk with *Lactobacillus reuteri*, the intestinal villi height and the intestinal villi to crypt depth ratio both increased by 60% or more, and the expression intensity of PIgR, mucin-2 and Occludin genes increased by 0.5 times, 4 times and 1.4 times, respectively. The FITC-F000 entering blood was reduced from 3.2 µg/mL to 2.1 µg/mL by *Lactobacillus reuteri* treatment (FIG. 11), indicating that the intestinal tissue structure and mucosal integrity was improved. According to the method of Example 4, the mouse crypts were isolated and cultured, and it was found that the ability of killing *Salmonella* of mouse crypts treated with *Lactobacillus reuteri* was significantly higher than that of the control ($p<0.01$, FIG. 12). *Lactobacillus reuteri* Fn041 also significantly enhanced the expression of several genes related to the antimicrobial peptide pathway in the intestinal mucosa of the dams, and increased the expression intensity of a-defesin, MyD88, RegIII-gamma, CRS1C and TLR2 by 3.5 times, 0.25 times, 0.3 times, 3.1 times and 2.2 times respectively. In the receptor, TLR2, TLR4 and TLR9 recognized bacterial peptidoglycan/lipoteichoic acid, lipopolysaccharide and CpG unmethylated DNA respectively, and only TRL2 expression was significantly up-regulated, indicating that *Lactobacillus reuteri* mainly stimulated the expression of antibacterial peptides through cytopeptidoglycan/lipoteichoic acid.

Example 7 Prevention of *Salmonella* Infection with *Lactobacillus reuteri* FN041

Six-week-old male C57BL/6J mice without specific pathogen were divided into three groups (30 mice in each group): (1) control group: treated with 0.1 mL of phosphate buffer through intragastric administration; (2) *Salmonella* infection group (SI): treated with 0.1 mL of phosphate buffer through intragastric administration for 10 days, and then infected with $1.0 \times 10^6$ *Salmonella typhimurium* SL1344 for 10 days every day; (3) *Lactobacillus reuteri* Fn041 intervention group (Fn041+SI): firstly treated with *Lactobacillus reuteri* Fn041 for 20 days ($1 \times 10^9$ CFU per mouse per day, suspended in 100 µL of phosphate buffer), and treated with *Salmonella* infection every day from the $11^{th}$ day to the $20^{th}$ day. The experiment was ended on the $21^{st}$ day.

As shown in FIG. 13, the survival rate of mice infected with *Salmonella* was only 40% on the $20^{th}$ day, but the survival rate of mice treated with *Lactobacillus reuteri* Fn041 increased to 70%, and there was a significant difference in the survival rate ($p<0.01$). The experiment further shows that Fn041 can enhance the resistance to pathogenic bacteria infection by enhancing the mucosal immunity of mice.

Example 8 Preparation of Formula Food with *Lactobacillus reuteri* Fn041

An de Man, Rogosa and Sharpe medium was inoculated with *Lactobacillus reuteri* Fn041, culturing was performed at 35-37° C. until the concentration of bacteria was $\geq 1 \times 10^3$ CFU/mL, and the bacterial cells were collected.

Optionally, a protective agent was added to the bacterial cells to prepare bacterial powder. The protective agent can be selected from monosaccharide, oligosaccharide, polysaccharide, polyol or a mixture thereof, such as trehalose, sorbitol, mannitol, etc.

The *Lactobacillus reuteri* Fn041 prepared by any one of the above methods was added to food in an amount of $1\times10^4$ to $1\times10^{11}$, preferably $1\times10^7$ to $1\times10^{11}$ cfu/unit mass (g) or unit volume (mL).

Optionally, the food also contains prebiotics, *Euglena* powder or *Euglena* extract, *pericarpium citri reticulatae* powder or *pericarpium citri reticulatae* extract, huckleberry fruit powder or huckleberry fruit extract, wolfberry fruit powder or wolfberry fruit extract, fructus cannabis powder, fructus cannabis protein, milk protein, and animal and plant hydrolyzed protein or peptide.

The prebiotics include, but are not limited to, inulin, fructooligosaccharides, short-chain fructooligosaccharides, galactooligosaccharides, human milk oligosaccharides or cow milk oligosaccharides or a combination of the above prebiotics.

What is claimed is:

1. A method of enhancing immunity, establishing an intestinal barrier, and/or strengthening the intestinal barrier, which comprises
    administering to a subject in need thereof *Lactobacillus reuteri* Fn041 or a composition comprising *L. reuteri* Fn041,
    wherein administering the *L. reuteri* Fn041 enhances immunity, establishes an intestinal barrier, and/or enhances an intestinal barrier in the subject,
    wherein the subject is an infant, pregnant woman, or lactating woman, and
    wherein the *L. reuteri* Fn041 has a preservation number GDMCC No. 60546.

2. The method according to claim 1, wherein the composition is a food or a medicine.

3. The method according to claim 1, wherein enhancing immunity, establishing the intestinal barrier, and/or strengthening the intestinal barrier comprises any one or more of:
    increasing mRNA expression and secretion of intestinal antibacterial peptide;
    promoting an increase in intestinal immunoglobulin A and intestinal IgA plasma cells;
    enhancing the barrier function of intestinal mucosae;
    enhancing the immunity of pregnant or lactating women;
    promoting development of the immune system of infants; and
    increasing *L. reuteri* in breast milk of the lactating women.

4. The method according to claim 1, wherein the subject is the infant, and wherein the infant is between 0 months and 36 months in age.

5. The method according to claim 1, wherein establishing the intestinal barrier or strengthening the intestinal barrier comprises decreasing a rate of pathogenic bacteria infection, and wherein the pathogenic bacteria comprises *Salmonella*.

6. The method according to claim 1, wherein the composition comprises an amount of $1 \times 10^4$ cfu to $1 \times 10^{11}$ cfu of the *L. reuteri* Fn041, and wherein the composition is administered once per day.

7. The method according to claim 1, wherein the composition comprises an amount of $1 \times 10^7$ cfu to $1 \times 10^{11}$ cfu of *L. reuteri* Fn041.

8. The method according to claim 1, wherein the composition comprises *L. reuteri* Fn041 in an amount of $1 \times 10^4$ cfu/g to $1 \times 10^{12}$ cfu/g dry matter.

9. The method according to claim 1, wherein the *L. reuteri* Fn041 is living or inactivated, and wherein the composition comprises fermentation products, or metabolites thereof, or a mixture of any one of the above.

10. The method according to claim 2, wherein the composition is the food.

11. The method according to claim 10, wherein the food is a fermented food that comprises one or more of fermented dairy products, fermented bean products, fermented fruit, and vegetable products.

12. The method according to claim 2, wherein the composition is the medicine and wherein the medicine is in a form of tablets, capsules, solid powder, or oral liquid.

13. The method according to claim 12, wherein the medicine further comprises a pharmaceutically acceptable carrier.

14. The method according to claim 12, wherein the composition further comprises one or more of: prebiotics, *Euglena* powder or extract, *pericarpium citri reticulatae* powder or extract, huckleberry fruit powder or extract, wolfberry fruit powder or extract, fructus cannabis powder, fructus cannabis protein, milk protein, animal hydrolyzed protein or peptide, and plant hydrolyzed protein or peptide.

15. The method according to claim 14, wherein the prebiotics comprise one or more of inulin, fructooligosaccharides, short-chain fructooligosaccharides, galactooligosaccharides, human milk oligosaccharides, and cow milk oligosaccharides.

16. A method of enhancing immunity, establishing an intestinal barrier, and/or strengthening the intestinal barrier, which comprises:
    administering to a subject in need thereof *Lactobacillus reuteri* Fn041 or a composition comprising *L. reuteri* Fn041,
    wherein administering the *L. reuteri* Fn041 enhances the immunity, establishes the intestinal barrier, and/or enhances the intestinal barrier in the subject,
    wherein the subject is an infant, pregnant woman, or lactating woman, and
    wherein the *L. reuteri* Fn041 has a preservation number GDMCC No. 60546,
    wherein the composition is a food, and
    wherein the food comprises fermented dairy products selected from one or more of fermented bean products, fermented fruit, and vegetable products.

* * * * *

```
                        SEQUENCE LISTING

<160> NUMBER OF SEQ ID NOS: 42

<210> SEQ ID NO 1
    <211> LENGTH: 23
    <212> TYPE: DNA
    <213> ORGANISM: Artificial sequence
    <220> FEATURE:
    <223> OTHER INFORMATION: Synthetic DNA

<400> SEQUENCE: 1
tgacgttgac atccgtaaag acc                                               23

<210> SEQ ID NO 2
    <211> LENGTH: 23
    <212> TYPE: DNA
    <213> ORGANISM: Artificial sequence
    <220> FEATURE:
    <223> OTHER INFORMATION: Synthetic DNA

<400> SEQUENCE: 2
ctcaggagga gcaatgatct tga                                               23

<210> SEQ ID NO 3
    <211> LENGTH: 21
    <212> TYPE: DNA
    <213> ORGANISM: Artificial sequence
    <220> FEATURE:
    <223> OTHER INFORMATION: Synthetic DNA

<400> SEQUENCE: 3
tacctcttga gccttgaact t                                                 21

<210> SEQ ID NO 4
    <211> LENGTH: 20
    <212> TYPE: DNA
    <213> ORGANISM: Artificial sequence
    <220> FEATURE:
    <223> OTHER INFORMATION: Synthetic DNA

<400> SEQUENCE: 4
cgtgctgatg tgccataata                                                   20

<210> SEQ ID NO 5
    <211> LENGTH: 20
    <212> TYPE: DNA
    <213> ORGANISM: Artificial sequence
    <220> FEATURE:
    <223> OTHER INFORMATION: Synthetic DNA

<400> SEQUENCE: 5
gccaaaaccc agaacaaaga                                                   20

<210> SEQ ID NO 6
    <211> LENGTH: 20
    <212> TYPE: DNA
```

```
<213> ORGANISM: Artificial sequence
<220> FEATURE:
<223> OTHER INFORMATION: Synthetic DNA

<400> SEQUENCE: 6
actgctctct cccacctcct                                               20

<210> SEQ ID NO 7
<211> LENGTH: 20
<212> TYPE: DNA
<213> ORGANISM: Artificial sequence
<220> FEATURE:
<223> OTHER INFORMATION: Synthetic DNA

<400> SEQUENCE: 7
gtgtggttga tccccaggag                                               20

<210> SEQ ID NO 8
<211> LENGTH: 20
<212> TYPE: DNA
<213> ORGANISM: Artificial sequence
<220> FEATURE:
<223> OTHER INFORMATION: Synthetic DNA

<400> SEQUENCE: 8
tcgcttgcca ttcactttgc                                               20

<210> SEQ ID NO 9
<211> LENGTH: 18
<212> TYPE: DNA
<213> ORGANISM: Artificial sequence
<220> FEATURE:
<223> OTHER INFORMATION: Synthetic DNA

<400> SEQUENCE: 9
cccaggccat gatggtga                                                 18

<210> SEQ ID NO 10
<211> LENGTH: 22
<212> TYPE: DNA
<213> ORGANISM: Artificial sequence
<220> FEATURE:
<223> OTHER INFORMATION: Synthetic DNA

<400> SEQUENCE: 10
tcatgcccac cacagagata at                                            22

<210> SEQ ID NO 11
<211> LENGTH: 20
<212> TYPE: DNA
<213> ORGANISM: Artificial sequence
<220> FEATURE:
<223> OTHER INFORMATION: Synthetic DNA

<400> SEQUENCE: 11
agtaaccgag gcctgtcctt                                               20

<210> SEQ ID NO 12
<211> LENGTH: 19
<212> TYPE: DNA
<213> ORGANISM: Artificial sequence
<220> FEATURE:
<223> OTHER INFORMATION: Synthetic DNA

<400> SEQUENCE: 12
gtcactcggc aactcagga                                                19
```

```
<210> SEQ ID NO 13
<211> LENGTH: 20
<212> TYPE: DNA
<213> ORGANISM: Artificial sequence
<220> FEATURE:
<223> OTHER INFORMATION: Synthetic DNA

<400> SEQUENCE: 13
cccagaaggg actgtgtatg                                               20

<210> SEQ ID NO 14
<211> LENGTH: 19
<212> TYPE: DNA
<213> ORGANISM: Artificial sequence
<220> FEATURE:
<223> OTHER INFORMATION: Synthetic DNA

<400> SEQUENCE: 14
tgcagacaca ctgctcaca                                                19

<210> SEQ ID NO 15
<211> LENGTH: 22
<212> TYPE: DNA
<213> ORGANISM: Artificial sequence
<220> FEATURE:
<223> OTHER INFORMATION: Synthetic DNA

<400> SEQUENCE: 15
atgaactacc cactaaccct gg                                            22

<210> SEQ ID NO 16
<211> LENGTH: 20
<212> TYPE: DNA
<213> ORGANISM: Artificial sequence
<220> FEATURE:
<223> OTHER INFORMATION: Synthetic DNA

<400> SEQUENCE: 16
tgtaggggaa tctccgtgct                                               20

<210> SEQ ID NO 17
<211> LENGTH: 20
<212> TYPE: DNA
<213> ORGANISM: Artificial sequence
<220> FEATURE:
<223> OTHER INFORMATION: Synthetic DNA

<400> SEQUENCE: 17
ggccacggta ttctggaagc                                               20

<210> SEQ ID NO 18
<211> LENGTH: 23
<212> TYPE: DNA
<213> ORGANISM: Artificial sequence
<220> FEATURE:
<223> OTHER INFORMATION: Synthetic DNA

<400> SEQUENCE: 18
gggcgtaact tgaatccgat cta                                           23

<210> SEQ ID NO 19
<211> LENGTH: 21
<212> TYPE: DNA
<213> ORGANISM: Artificial sequence
<220> FEATURE:
```

<223> OTHER INFORMATION: Synthetic DNA

<400> SEQUENCE: 19
ctttcggttg ctctttggtt g                                          21

<210> SEQ ID NO 20
<211> LENGTH: 19
<212> TYPE: DNA
<213> ORGANISM: Artificial sequence
<220> FEATURE:
<223> OTHER INFORMATION: Synthetic DNA

<400> SEQUENCE: 20
cgacagcaca agtcacagc                                             19

<210> SEQ ID NO 21
<211> LENGTH: 19
<212> TYPE: DNA
<213> ORGANISM: Artificial sequence
<220> FEATURE:
<223> OTHER INFORMATION: Synthetic DNA

<400> SEQUENCE: 21
ctcccgtggc ttctagtgc                                             19

<210> SEQ ID NO 22
<211> LENGTH: 22
<212> TYPE: DNA
<213> ORGANISM: Artificial sequence
<220> FEATURE:
<223> OTHER INFORMATION: Synthetic DNA

<400> SEQUENCE: 22
gccttagttt ggacaggatc tg                                         22

<210> SEQ ID NO 23
<211> LENGTH: 19
<212> TYPE: DNA
<213> ORGANISM: Artificial sequence
<220> FEATURE:
<223> OTHER INFORMATION: Synthetic DNA

<400> SEQUENCE: 23
cccatcccca ggagtcttg                                             19

<210> SEQ ID NO 24
<211> LENGTH: 21
<212> TYPE: DNA
<213> ORGANISM: Artificial sequence
<220> FEATURE:
<223> OTHER INFORMATION: Synthetic DNA

<400> SEQUENCE: 24
accatgacta ggggcactgt a                                          21

<210> SEQ ID NO 25
<211> LENGTH: 18
<212> TYPE: DNA
<213> ORGANISM: Artificial sequence
<220> FEATURE:
<223> OTHER INFORMATION: Synthetic DNA

<400> SEQUENCE: 25
aaaatgtcgt tcaaggag                                              18

```
<210> SEQ ID NO 26
<211> LENGTH: 18
<212> TYPE: DNA
<213> ORGANISM: Artificial sequence
<220> FEATURE:
<223> OTHER INFORMATION: Synthetic DNA

<400> SEQUENCE: 26
ttgctgaaga ggactgtt                                                      18

<210> SEQ ID NO 27
<211> LENGTH: 21
<212> TYPE: DNA
<213> ORGANISM: Artificial sequence
<220> FEATURE:
<223> OTHER INFORMATION: Synthetic DNA

<400> SEQUENCE: 27
ggaacaaaca gcctgagaca c                                                  21

<210> SEQ ID NO 28
<211> LENGTH: 22
<212> TYPE: DNA
<213> ORGANISM: Artificial sequence
<220> FEATURE:
<223> OTHER INFORMATION: Synthetic DNA

<400> SEQUENCE: 28
caagggataa gaacgctgag aa                                                 22

<210> SEQ ID NO 29
<211> LENGTH: 18
<212> TYPE: DNA
<213> ORGANISM: Artificial sequence
<220> FEATURE:
<223> OTHER INFORMATION: Synthetic DNA

<400> SEQUENCE: 29
ggtgtggaac atcattct                                                      18

<210> SEQ ID NO 30
<211> LENGTH: 18
<212> TYPE: DNA
<213> ORGANISM: Artificial sequence
<220> FEATURE:
<223> OTHER INFORMATION: Synthetic DNA

<400> SEQUENCE: 30
atacggttgg agatcaag                                                      18

<210> SEQ ID NO 31
<211> LENGTH: 25
<212> TYPE: DNA
<213> ORGANISM: Artificial sequence
<220> FEATURE:
<223> OTHER INFORMATION: Synthetic DNA

<400> SEQUENCE: 31
tggcatgcct ccatcatagt taacc                                              25

<210> SEQ ID NO 32
<211> LENGTH: 23
<212> TYPE: DNA
<213> ORGANISM: Artificial sequence
<220> FEATURE:
<223> OTHER INFORMATION: Synthetic DNA
```

<400> SEQUENCE: 32
gtcagaaaca accaccacca tgc								23

<210> SEQ ID NO 33
<211> LENGTH: 20
<212> TYPE: DNA
<213> ORGANISM: Artificial sequence
<220> FEATURE:
<223> OTHER INFORMATION: Synthetic DNA

<400> SEQUENCE: 33
aggcttctgg gccttatgtg								20

<210> SEQ ID NO 34
<211> LENGTH: 21
<212> TYPE: DNA
<213> ORGANISM: Artificial sequence
<220> FEATURE:
<223> OTHER INFORMATION: Synthetic DNA

<400> SEQUENCE: 34
tgcttctctc gccaggaata c								21

<210> SEQ ID NO 35
<211> LENGTH: 24
<212> TYPE: DNA
<213> ORGANISM: Artificial sequence
<220> FEATURE:
<223> OTHER INFORMATION: Synthetic DNA

<400> SEQUENCE: 35
tgctcttcaa gatgtagccc aacg								24

<210> SEQ ID NO 36
<211> LENGTH: 22
<212> TYPE: DNA
<213> ORGANISM: Artificial sequence
<220> FEATURE:
<223> OTHER INFORMATION: Synthetic DNA

<400> SEQUENCE: 36
tggagcttgg gtggtgattg ca								22

<210> SEQ ID NO 37
<211> LENGTH: 24
<212> TYPE: DNA
<213> ORGANISM: Artificial sequence
<220> FEATURE:
<223> OTHER INFORMATION: Synthetic DNA

<400> SEQUENCE: 37
gcatggaatc tgggtcaaga taac								24

<210> SEQ ID NO 38
<211> LENGTH: 25
<212> TYPE: DNA
<213> ORGANISM: Artificial sequence
<220> FEATURE:
<223> OTHER INFORMATION: Synthetic DNA

<400> SEQUENCE: 38
agaaggaaga gcaatcaagg ctaag								25

<210> SEQ ID NO 39
<211> LENGTH: 22

```
<212> TYPE: DNA
<213> ORGANISM: Artificial sequence
<220> FEATURE:
<223> OTHER INFORMATION: Synthetic DNA

<400> SEQUENCE: 39
ttcctgtcct ccatgatcaa aa                                              22

<210> SEQ ID NO 40
<211> LENGTH: 21
<212> TYPE: DNA
<213> ORGANISM: Artificial sequence
<220> FEATURE:
<223> OTHER INFORMATION: Synthetic DNA

<400> SEQUENCE: 40
catccacctc tgttgggttc a                                               21

<210> SEQ ID NO 41
<211> LENGTH: 24
<212> TYPE: DNA
<213> ORGANISM: Artificial sequence
<220> FEATURE:
<223> OTHER INFORMATION: Synthetic DNA

<400> SEQUENCE: 41
atcatccagg tgattcccag ccat                                            24

<210> SEQ ID NO 42
<211> LENGTH: 24
<212> TYPE: DNA
<213> ORGANISM: Artificial sequence
<220> FEATURE:
<223> OTHER INFORMATION: Synthetic DNA

<400> SEQUENCE: 42
ttccgggtct ccaaaggaaa caga                                            24
```